(12) United States Patent
Zhang

(10) Patent No.: US 8,833,155 B2
(45) Date of Patent: Sep. 16, 2014

(54) MEASUREMENT APPARATUS FOR MEASURING ELASTICITY COEFFICIENT OF COIL SPRING

(75) Inventor: Bing-Jun Zhang, Shenzhen (CN)

(73) Assignees: Hong Fu Jin Precision Industry (ShenZhen) Co., Ltd., Shenzhen (CN); Hon Hai Precision Industry Co., Ltd., New Taipei (TW)

( * ) Notice: Subject to any disclaimer, the term of this patent is extended or adjusted under 35 U.S.C. 154(b) by 66 days.

(21) Appl. No.: 13/593,530

(22) Filed: Aug. 24, 2012

(65) Prior Publication Data
US 2013/0276545 A1 Oct. 24, 2013

(30) Foreign Application Priority Data

Apr. 19, 2012 (CN) .......................... 2012 1 0116036

(51) Int. Cl.
*G01L 1/04* (2006.01)
(52) U.S. Cl.
USPC .............................................. 73/161; 73/788
(58) Field of Classification Search
USPC .................................. 73/161, 760, 788, 796
See application file for complete search history.

(56) References Cited

U.S. PATENT DOCUMENTS

| | | | | |
|---|---|---|---|---|
| 4,603,567 A | * | 8/1986 | Smith et al. .................... | 72/16.9 |
| 5,058,888 A | * | 10/1991 | Walker et al. ..................... | 482/8 |
| 5,877,405 A | * | 3/1999 | Champaigne ................ | 73/11.02 |
| 6,094,980 A | * | 8/2000 | Larson et al. ................... | 73/161 |
| 7,624,512 B2 | * | 12/2009 | Zhang et al. ................. | 33/555.1 |
| 8,240,219 B2 | * | 8/2012 | Zhang ............................ | 73/838 |

* cited by examiner

*Primary Examiner* — Max Noori
(74) *Attorney, Agent, or Firm* — Novak Druce Connolly Bove + Quigg LLP

(57) ABSTRACT

A measurement apparatus includes a workbench, a loading mechanism fixed to the workbench, a deformation measuring mechanism, and a stress meter. The deformation measuring mechanism includes a slide beam, and a displacement meter. The loading mechanism includes a guiding shaft extending through a to-be-tested coil spring. A measuring pole of the stress meter, the sliding beam, and the guiding shaft are coaxial. Opposite ends of the coil spring are respectively abutted the slide beam and the loading mechanism. A measuring pole of the displacement meter is connected to the sliding beam. When the stress meter slides towards the slide beam, the displacement of the detecting pole of the displacement member is equal to a change of a length of the coil spring, and recorded by the displacement meter, and a value of a force applied to the coil spring is recorded by the stress meter.

8 Claims, 3 Drawing Sheets

US 8,833,155 B2

MEASUREMENT APPARATUS FOR MEASURING ELASTICITY COEFFICIENT OF COIL SPRING

BACKGROUND

1. Technical Field

The present disclosure relates to a measurement apparatus for measuring an elasticity coefficient of a coil spring.

2. Description of Related Art

Coil springs are widely used in electronic products. The elasticity coefficient of a coil spring, which is defined as the ratio of the stress applied to coil spring to the change of the length of the coil spring, is critical in determining the usage of the coil spring. Traditionally, the elasticity coefficient of a coil spring is measured in laboratory with a precision device. However, the measurement period could be too long to satisfy the demand for quality control in mass production of electronic products.

BRIEF DESCRIPTION OF THE DRAWINGS

Many aspects of the present embodiments can be better understood with reference to the following drawings. The components in the drawings are not necessarily drawn to scale, the emphasis instead being placed upon clearly illustrating the principles of the present embodiments. Moreover, in the drawings, all the views are schematic, and like reference numerals designate corresponding parts throughout the several views.

DETAILED DESCRIPTION

The present disclosure, including the accompanying drawings, is illustrated by way of examples and not by way of limitation. It should be noted that references to "an" or "one" embodiment in this disclosure are not necessarily to the same embodiment, and such references mean at least one.

Figure 1:
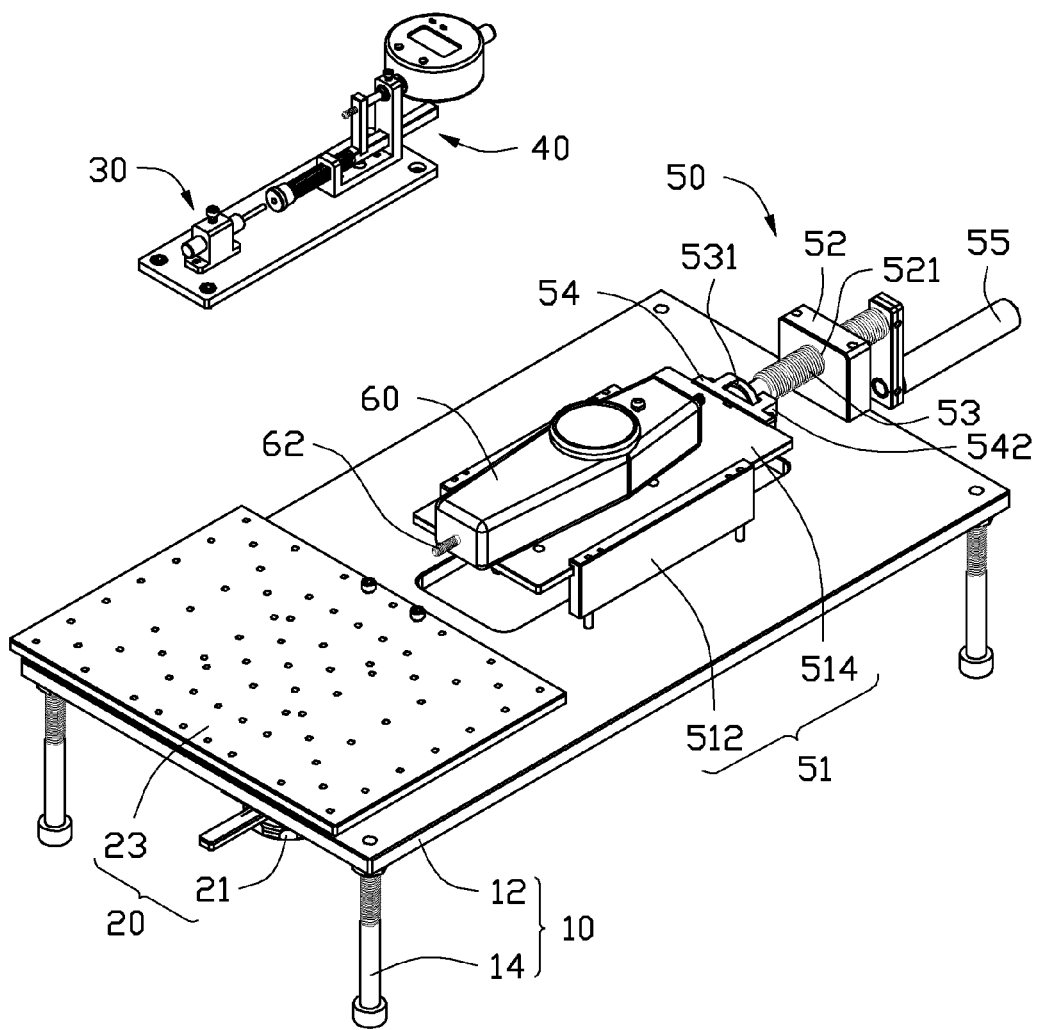
FIG. 1 is an exploded, isometric view of an embodiment of a measurement apparatus, which includes a workbench, a mounting member, a loading mechanism, a deformation measuring mechanism, a driving mechanism, and a stress meter.

Referring to FIG. 1, an exemplary embodiment of a measurement apparatus is shown. The measuring apparatus includes a workbench 10, a mounting member 20, a loading mechanism 30, a deformation measuring mechanism 40, a driving mechanism 50, and a stress meter 60.

The workbench 10 includes a rectangular, horizontally-oriented support plate 12 and two support posts 14 respectively extending down from the four corners of the support plate 12.

The mounting member 20 includes an elevating member 21 mounted to a first end of the support plate 12, and a mounting plate 23 fixed to the elevating member 21, over the support plate 12. The elevating member 21 can drive the mounting plate 23 to move up and down.

Figure 2:
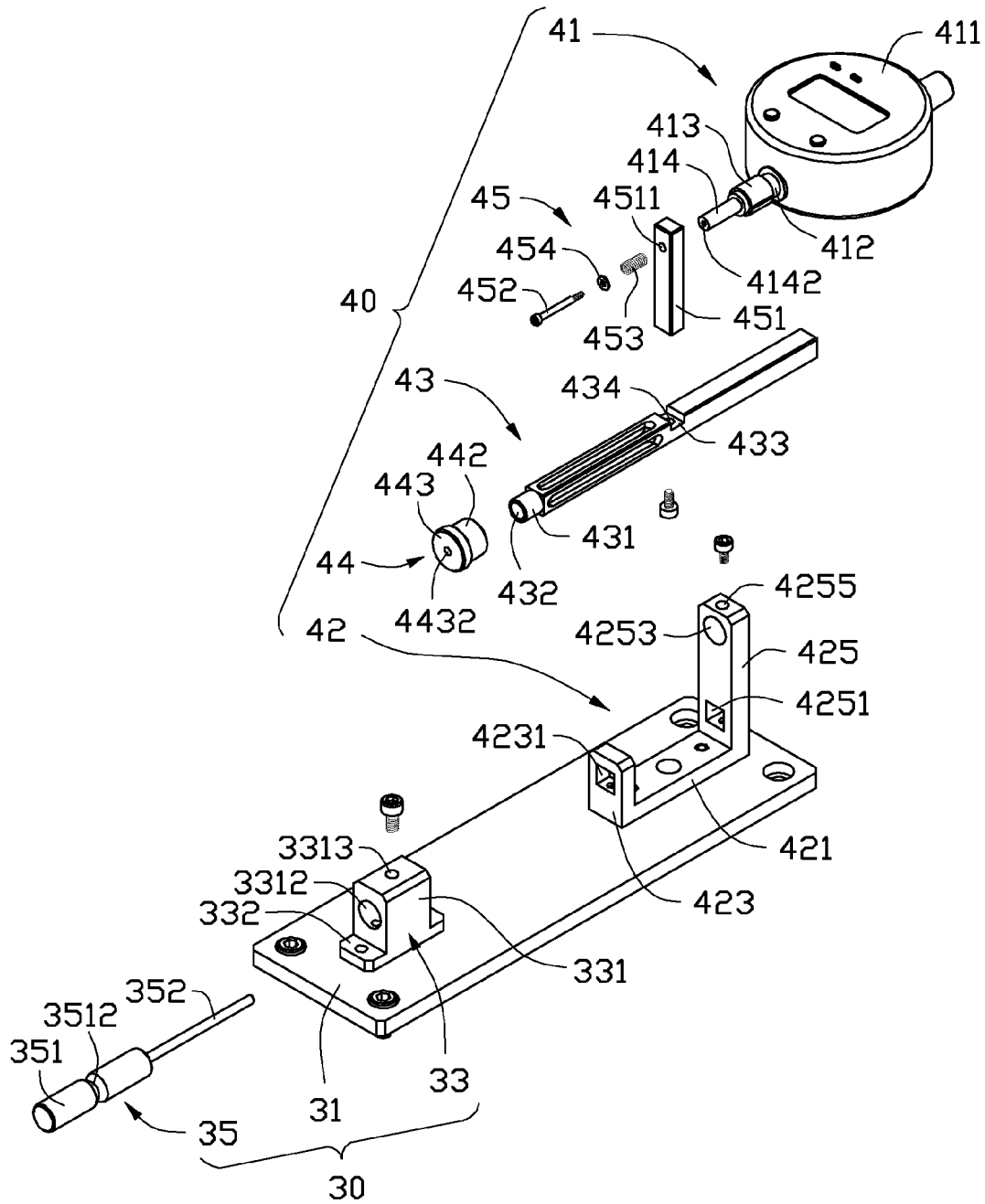
FIG. 2 is an exploded, isometric view of the loading mechanism and the deformation measuring mechanism of FIG. 1.

Referring to FIG. 2, the loading mechanism 30 of the embodiment is shown. The loading mechanism 30 includes a bottom plate 31, a locating member 33, and a guiding shaft 35. The locating member 33 includes a rectangular main body 331, and two fixing tabs 332 extending from bottoms of two opposite sides of the main body 331. A through hole 3312 is defined in the main body 331, extending through the opposite sides of the main body 331. A fastening hole 3313 is defined in a top of the main body 331. Each of the tabs 332 defines a fixing hole for a screw extending through the fixing hole to fix the locating member 331 to a first end of the bottom plate 31. The guiding shaft 35 includes a connection portion 351, and a guiding portion 352 extending from and end of the guiding shaft 35. A diameter of the connection portion 351 is greater than a diameter of the guiding portion 352. A circular groove 3512 is defined in a circumference of the connection portion 351.

The deformation measuring mechanism 40 includes a displacement meter 41, a guiding member 42, a slide beam 43, an abutting member 44, and a connecting member 45.

The displacement meter 41 includes a dial plate 411, a measuring pole 414 telescopingly extending from a side of the dial plate 411, a sleeve 412 protruding from the side of the dial plate 411 and sleeving on the measuring pole 414, a deformable bushing 413 sleeving on the sleeve 412. In use, a stretching distance of the measuring pole 414 is recorded by the displacement meter 41 and shown on the dial plate 411. A connection hole 4142 is axially defined in a distal end of the measuring pole 414.

The guiding member 42 is substantially U-shaped, and includes a fixing portion 421 fixed on a second end of the bottom plate 31 far away from the first end of the bottom plate 31, a first guiding arm 423 extending up from a first end of the fixing portion 421 facing the locating member 331, and a second guiding arm 425 extending up from a second end of the fixing portion 421 away from the locating member 331. The first guiding arm 423 defines a first guiding hole 4231. The second guiding arm 425 defines a second guiding hole 4251 adjacent to the fixing portion 421, a mounting hole 4253 adjacent to a top of the second guiding arm 425, and a fastening hole 4255 in the top of the second guiding arm 425 and communicating with the mounting hole 4253. The first guiding hole 4231, the second guiding hole 4251, and the through hole 3312 are coaxial.

The slide beam 43 forms a coupling portion 431 at an end of the slide beam 43. The slide beam 43 defines a receiving hole 432 axially extending through the end of the coupling portion 431. The slide beam 43 defines a positioning notch 433 in a middle of the slide beam 43, and a fastening hole 434 in a bottom wall bounding the positioning notch 433.

The abutting member 44 includes a coupling ring 442, and a round end plate 443 formed on an end of the coupling ring 44. The end plate 443 defines a through hole 4432 in a center of the end plate 443.

The connecting member 45 includes a connecting pole 451, a bolt 452, a resilient member 453, and a washer 454. The connecting pole 451 defines a through hole 4511 adjacent to a top end of the connecting pole 451. In one embodiment, the resilient member 453 is a coil spring.

Referring to FIG. 1, the driving mechanism 50 of the embodiment is shown. The driving mechanism 50 includes a base mount 51, a supporting block 52, a threaded pole 53, an engaging member 54, and a handle 55. The base mount 51 includes two opposite side boards 512 perpendicularly fixed to the supporting plate 12, and a conveying board 514 slidably mounted between the side boards 512 in a direction parallel to the supporting plate 12. The supporting block 52 is mounted on a second end of the supporting plate 12 away from the mounting member 20. The base mount 51 is located between the mounting member 20 and the supporting block 52. The supporting block 52 defines a threaded hole 521 extending in a direction parallel to the supporting plate 12. The threaded pole 53 engagingly extends through the threaded hole 521 of the supporting block 52. A disc-like connecting portion 531 is formed on a first end of the threaded pole 53 facing the base mount 51. The handle 55 is fixed to a second end of the threaded pole 53 opposite to the connecting portion 531. The engaging member 54 is fixed to an end of the conveying board 514 facing the supporting block 52, and forms two opposite L-shaped hooks 542. The connecting portion 531 is rotatably embraced between the hooks 542.

The stress meter 60 is fixed on the conveying board 514, and includes a measure pole 62 extending towards the mounting member 20, parallel to the supporting plate 12. The stress meter 60 records and shows a value of the force axially applied to the measure pole 62.

Figure 3:
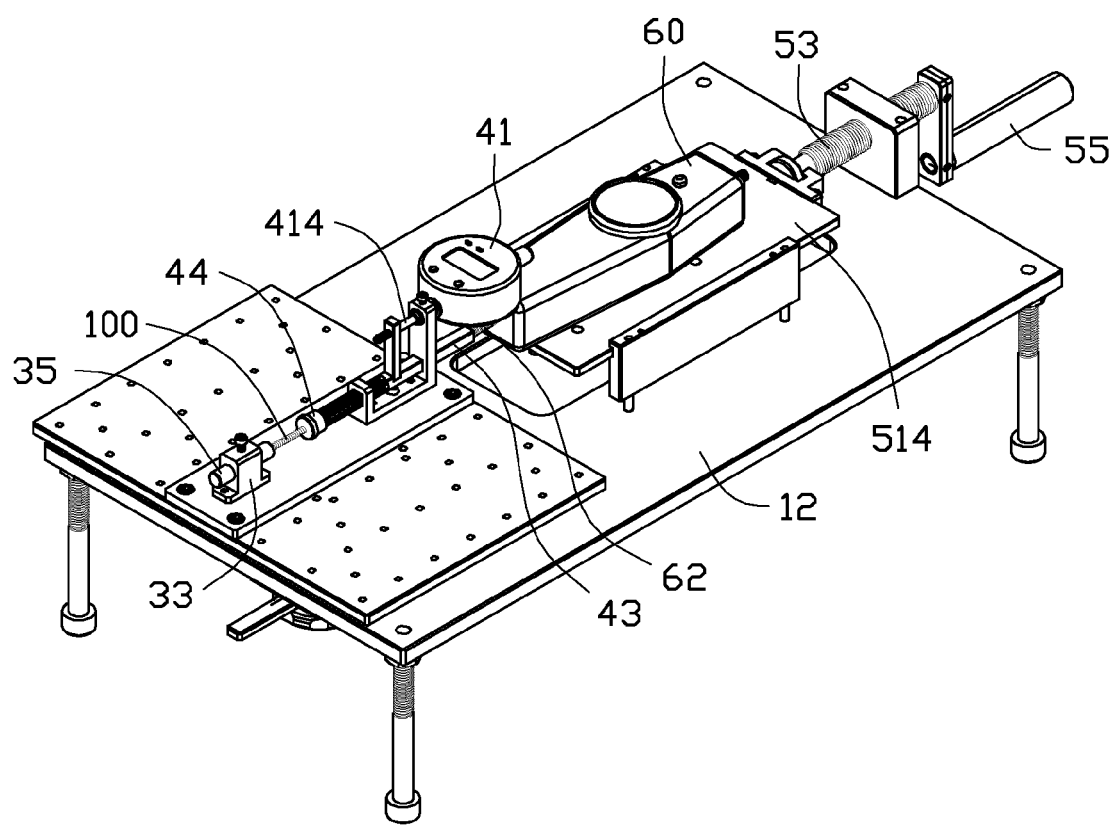
FIG. 3 is an assembled, isometric view of the apparatus of FIG. 1, and a coil spring to be measured.

Referring to FIGS. 1 and 3, in assembly, the slide beam 43 extends through the first guiding hole 4231 and the second guiding hole 4251 of the guiding member 42, with the coupling portion 431 placed between the guiding member 42 and the locating member 33. The coupling ring 442 of the abutting member 44 sleeves on the coupling portion 431, with the through hole 4432 of the end plate 443 aligning with the receiving hole 432 of the slide beam 43. A bottom end of the connecting pole 451 is engaged in the positioning notch 433 of the slide beam 43. A screw extends through the fastening hole 434 of the slide beam 43 and is fastened to the bottom end of the connecting pole 451. Therefore, the connecting pole 451 is fixed to the slide beam 43. The bushing 413 is received in the mounting hole 4253 of the guiding member 42. A screw engages in the fastening hole 4255 and abuts the bushing 413 to fix the bushing 413 to the guiding member 42. At the same time, the bushing 413 is deformed to tightly hold the sleeve 412, to fix the dial plate 411 of the displacement meter 41 to the guiding member 42. The measure pole 414 abuts the connecting pole 451, with the connection hole 4142 of the measuring pole 414 aligning with the through hole 4511. The bolt 452 sequentially extends through the washer 454, the resilient member 453, and the through hole 4511, to be fastened in the connection hole 4142. The resilient member 453 biases the bolt 452 away from the connecting pole 451, to keep the distal end of the measuring pole 414 abutting the connecting pole 451. The bottom plate 31 is mounted on the mounting plate 23 of the mounting member 20. The elevating member 21 is manipulated to adjust a position of the bottom plate 31, thereby making the slide beam 43 coaxial with the measure pole 62 of the stress meter 60.

In measuring, a coil spring 100 to be tested is placed around the guiding portion 352 of the guiding shaft 35. The coil spring 100 and the guiding shaft 35 extend through the through hole 3312 of the locating member 33 from a side away from the slide beam 43. The connection portion 351 of the guiding shaft 35 is received in the through hole 3312, with the circular groove 3512 of the connection portion 351 aligning with the fastening hole 3313 of the locating member 33. A screw engagingly extends through the fastening hole 3313 and engages in the circular groove 3512 to retain the guiding shaft 35 to the locating member 33. The guiding shaft 35 is coaxial with the slide beam 43, with the guiding portion 352 aligning with the through hole 4432 of the end plate 443. The coil spring 100 is slid along the guiding portion 352 to make a first end of the coil spring 100 abut the connection portion 351. The handle 55 is manipulated to drive the threaded pole 53 to rotate in the threaded hole 521. Because of the engagement between the threaded pole 53 and the threaded hole 521, the threaded pole 53 moves axially towards the coil spring 100 with the rotation of the threaded pole 53. Therefore, the threaded pole 53 drives the conveying board 514 and the stress meter 60 to move towards the coil spring 100. The measuring pole 62 pushes the slide beam 43 to make the connection portion 351 to be inserted into the through hole 4432, until the end plate 443 contacts with a second end of the resilient member 100 opposite to the locating member 33. The stress meter 60 and the displacement meter 41 are initialized.

The handle 55 is manipulated to drive the stress meter 60 and the slide beam 43 to further slide towards the coil spring 100. The measuring pole 414 slides in synchronization with the slide beam 43. At the same time, the coil spring 100 is deformed by the sliding of the slide beam 43. Therefore, a change of length 100 is equal to the a sliding distance of the slide beam 43, which is further equal to a sliding distance of the measure pole 414, recorded by the displacement meter 41. A value of a force applied to the coil spring 100 by the slide beam 43 is equal to a value of a force applied to the slide beam 43 by the measuring pole 62, and recorded by the stress meter 60. Therefore, an elasticity coefficient of the coil spring 100 can be calculated based on the values shown on the displacement meter 41 and the stress meter 60.

It is to be understood, however, that even though numerous characteristics and advantages of the embodiments have been set forth in the foregoing description, together with details of the structure and function of the embodiments, the present disclosure is illustrative only, and changes may be made in details, especially in matters of shape, size, and arrangement of parts within the principles of the embodiments to the full extent indicated by the broad general meaning of the terms in which the appended claims are expressed.

What is claimed is:

1. A measurement apparatus for measuring an elasticity coefficient of a coil spring, comprising:
    a workbench comprising a supporting plate;
    a loading mechanism comprising a guiding shaft fixed to the supporting plate, the guiding shaft comprising a connection portion abutting one of two opposite ends of the coil spring when the coil spring is being measured, and a guiding portion extending in parallel with the supporting plate and through the coil spring;
    a deformation measuring mechanism comprising a guiding member mounted on the supporting plate, a slide beam slidably connected to the guiding member and coaxial with the guiding shaft, a connecting pole secured to the slide beam, an abutting member fixed to the slide beam and abutting the other end of the coil spring, and a displacement meter comprising a dial plate fixed to the guiding member, and a measure pole telescopingly extending from the dial plate and fixed to the connecting pole, wherein a stretch distance of the measure pole is recorded by the displacement meter and shown on the dial plate;
    a stress meter slidably mounted on the supporting plate, and comprising a measure pole extending towards and coaxial with the slide beam, wherein a value of a force applied to the measure pole of the stress meter is recorded by and shown on the stress meter;
    a driving mechanism mounted to the supporting plate and connected to the stress meter to drive the stress meter to slide relative to the supporting plate along an axial direction of the measure pole of the stress meter; and
    a mounting member mounted to the supporting plate, wherein the loading mechanism further comprises a bottom plate fixed to the mounting member, and a locating member fixed to the bottom plate, the connection portion of the guiding shaft is secured to the locating member.

2. The measurement apparatus of claim 1, wherein the slide beam axially defines a receiving hole in an end of the slide beam adjacent to the guiding shaft, the abutting member comprises a coupling ring sleeving on the slide beam, and an end plate formed on an end of the coupling ring, the end plate defines a through hole aligning with the receiving hole of the slide beam, the guiding shaft extends through the through hole of the end plate and is received in the receiving hole of the slide beam.

3. The measurement apparatus of claim 1, wherein the mounting member comprises an elevating member mounted to the supporting plate, and a mounting plate fixed to the elevating member, and capable of being driven up and down by the elevating member.

4. The measurement apparatus of claim 1, wherein the guiding member of the deformation measuring mechanism comprises a fixing portion fixed on the bottom plate, a first guiding arm extending up from a first end of the fixing portion adjacent to the locating member, and a second guiding arm extending up from a second end of the fixing portion far away from the locating member, the first guiding arm defines a first guiding hole, the second guiding arm defines a second guiding hole aligning with the first guiding hole, the slide beam slidably extending through the first and the second guiding holes.

5. The measurement apparatus of claim 4, wherein the second guiding arm is taller than the first guiding arm, the second guiding arm further defines a mounting hole above the second guiding hole, the dial plate of the displacement meter is fixed to a side of the second guiding arm, the measure pole of the displacement meter slidably extending through the mounting hole of the second guiding arm.

6. The measurement apparatus of claim 5, wherein the connecting pole perpendicularly extends up from the slide beam, and is arranged between the first and second guiding arms.

7. The measurement apparatus of claim 6, wherein the connecting pole defines a through hole adjacent to a top of the connecting pole, a connection hole is defined in a distal end of the measure pole of the displacement meter, the measure pole of the displacement meter is fixed to the connecting pole with a bolt sequentially extending through a bushing, a resilient member, and the through hole of the connecting pole, to be fastened in the connection hole of the measure pole of the displacement meter.

8. The measurement apparatus of claim 1, wherein the driving mechanism comprises a conveying board slidably mounted to the supporting plate in a direction parallel to the supporting plate and fixed to the stress meter, a supporting block fixed to the supporting plate, a threaded pole with first end rotatably connected to the conveying board, and a handle fixed to a second end of the threaded pole, the supporting block defines a threaded hole extending in parallel with the slide beam, the threaded pole engagingly extends through the threaded hole of the supporting block.

* * * * *